Jan. 29, 1957 W. E. LAMMERTS Plant Pat. 1,557
ROSE PLANT
Filed March 30, 1956
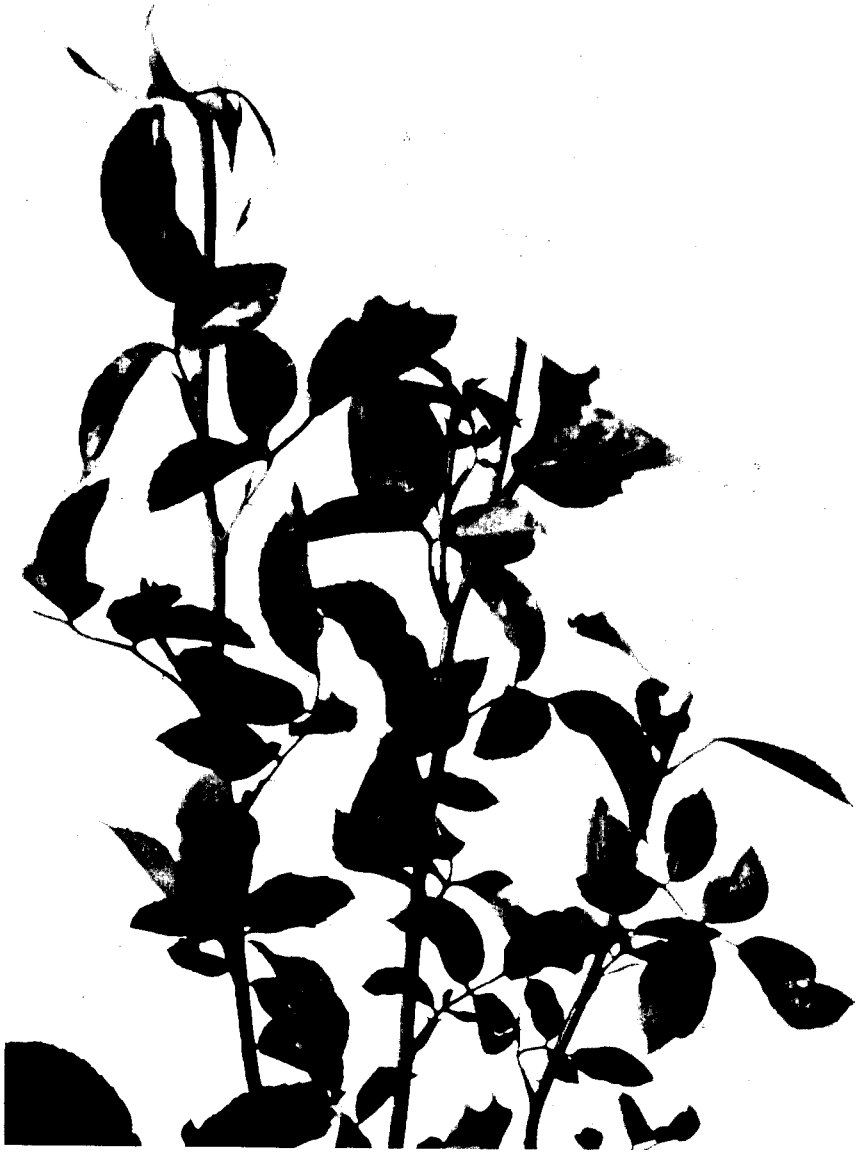
Inventor.
W. E. Lammerts
By: Robb & Robb
Attorneys.

United States Patent Office

Plant Pat. 1,557
Patented Jan. 29, 1957

1,557

ROSE PLANT

Walter E. Lammerts, Livermore, Calif., assignor, by mesne assignments, to Germain's, Inc., Van Nuys, Calif., a corporation of California Application March 30, 1956, Serial No. 575,297

1 Claim. (Cl. 47—61)

The present invention relates to a new and distinct variety of rose plant of the everblooming pillar rose type and hybrid Wichuraiana class, which was originated by me by crossing the variety "Charlotte Armstrong" (Plant Patent No. 455) with the variety "Captain Thomas" (Plant Patent No. 393).

As the result of this cross, I have produced a new rose variety which generally resembles the variety "High Noon" (Plant Patent No. 704) in respect to its very vigorous and pillar type of growth, attaining a height of from 6 to 8 feet or more, and in respect to its everblooming habit of growth, but which is distinguished from "High Noon," as well as from its parents, by the following combination of outstanding characteristics:

(1) Its winter-hardiness;

(2) Its relatively large and glossy leaves and the abundance thereof, particularly near the base of the plant;

(3) Its relatively large, long buds which are urn-shaped like the buds of "High Noon," at first, but which become long-pointed and high-centered in form as the flowers open;

(4) The relatively light color of the buds which are Empire Yellow in general color tonality, as distinguished from the darker Lemon Yellow color of the buds of "High Noon" which are usually heavily tinged with Indian Orange pigmentation, as compared with only a slight tinge of Maize Yellow in the buds of the new variety; and (5) The very uniform Empire Yellow general color tonality of the open flowers which are lighter in color than the usual Canary Yellow of "High Noon."

The foregoing characteristics of my new variety represent a unique combination in a rose of this class, and differentiate the new variety from all others of which I am aware. Asexual reproduction of the new variety by both grafting and budding, as performed by me at Livermore, California, shows that the aforesaid characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology in accordance with the Horticultural Color Chart of the British Color Council, except where general color terms of ordinary dictionary significance are obvious:

Type: Half-hardy; tall; pillar; for garden decoration.
Class: Hybrid Wichuraiana.
Breeding: Seedling.
*Seed parent.*—"Charlotte Armstrong."
*Pollen parent.*—"Captain Thomas."
Propagation: Holds its distinguishing characteristics through succeeding propagations by both grafting and budding.

FLOWER

Locality where grown and observed: Livermore, California.
Flowers borne: Sometimes singly, sometimes 2 to 5 per stem, and sometimes in compound, irregular clusters of from 10 to 15 flowers; on strong stems of medium length.
Quantity of bloom: Abundant, outdoors.
Continuity: Continuous.
Fragrance: Moderate. Nature—centifolia.
Bud:
*Peduncle.*—Medium length; medium caliper; erect; stiff; entirely smooth; with few Red, gland-tipped hairs and a very fine Gray pubescence of many very minute Gray hairs. Color—Fern Green, Plate 0862, tinged with anthocyanin on exposed sunny side.
*Before calyx breaks.*—Size—medium. Form—short; from urn-shape to pointed; without foliaceous appendages on the surface of the bud; with a foliaceous part of only one sepal extending about ¼ inch beyond the tip of the bud, and with every other sepal (3 of 5) having 3 or 4 lance-shaped foliaceous appendages on margin from ⅛ to ¼ inch long. Color—Empire Yellow, Plate 603, tinged with Maize Yellow, Plate 607/2 between sepals.
*As calyx breaks.*—Color—Empire Yellow, Plate 603.
*As first petal opens.*—Size—medium. Form—long; pointed; high-centered. Color: Outside—Empire Yellow, Plate 603; inside—Empire Yellow, Plate 603.
*Opening.*—Opens up well; opening is retarded by cold weather.
Bloom:
*Size (when fully open).*—Large; from 4 inches to 4½ inches.
*Petalage.*—Double; from 20 to 35 petals; arranged regularly.
*Form.*—High-centered at first, but becoming flat; petals being at first loosely rolled inward, but later becoming loosely rolled outward at maturity.
Petals:
*Texture.*—Medium heavy; with both inside and outside satiny.
*Shape.*—Outside—obovate, with apex having 1 or 2 notches. Intermediate—obovate-lanceolate, with apex having 1 notch. Inside—obovate-lanceolate, with apex having 1 notch.

This description of a newly opened flower was made from a rose grown outdoors in the month of September, at Livermore, California.

*Color.*—Outer petal: Outside surface—generally Empire Yellow, Plate 603/2, with outer margin occasionally tinged with Maize Yellow, Plate 607/2, and shading to Empire Yellow, Plate 603 near base of petal; inside surface—Empire Yellow, Plate 603/1, shading to Empire Yellow, Plate 603 near base of petal. Intermediate petal: Outside surface—Aureolin, Plate 3/1 at margin, shading to Aureolin, Plate 3 near base, and occasionally tinged with Maize Yellow, Plate 607/2 on outer margin; inside surface—Empire Yellow, Plate 603/1, shading to Empire Yellow, Plate 603 near base. Inner petal: Outside surface—Aureolin, Plate 3/1, shading to Aureolin, Plate 3 at base; inside surface—Empire Yellow, Plate 603.

This description was made from a rose that was open for 3 days outdoors in the month of September, at Livermore, California:

*Color.*—Outer petal: Outside surface—Canary Yellow, Plate 2/3; inside surface—Canary Yellow, Plate 2/3. Inner petal: Outside surface—Empire Yellow, Plate 603/2; inside surface—Empire Yellow, Plate 603/2.

*General color effect.*—Very uniform. Newly opened flower—Empire Yellow, Plate 603. 3-days open—Canary Yellow, Plate 2/3.

*Behavior.*—Drop off cleanly; fading to lighter Yellow color; hot weather causes size of flowers to be smaller, and flowers open more rapidly, with accompanying acceleration of fading.

*Flower longevity.*—On bush in garden—2 days in September. Cut roses grown outdoors and kept at living-room temperatures—2 days in September.

REPRODUCTIVE ORGANS

Stamens: Medium number; arranged irregularly about pistils; mixed with petaloids.

Filaments: Short; a few almost twice the length of the remainder and therefore supporting anthers almost ¼ inch above general level of stigmas; most with anthers; most anthers at same level as stigmas. Color—Blood Red, Plate 820 at base, shading through Nasturtium Orange, Plate 610 to Maize Yellow, Plate 607 at junction with anthers.

Anthers: Small; open at various times. Color—Straw Yellow, Plate 604/2.

Pollen: Moderate. Color—Yellow.

Pistils: Medium number.

Styles: Uneven; medium length; thin; loosely columnar.

Stigma: Color—Straw Yellow, Plate 604/2.

Ovaries: All enclosed in calyx tube.

Hips: Globular; with inconspicuous neck; very smooth; walls moderately thick and fleshy. Color—Yellow.

Sepals: Falling soon; moderately long; spear-shaped; recurved. Color—Lavendar Green, Plate 000761/1.

Seeds: Many; medium size.

PLANT

Foliage:

*Leaves.*—Compound of 3 to 5 leaflets; medium large; very moderately leathery; glossy.

*Leaflets.*—Shape—from round to elongate oval, with apex mucronate. Base—round. Margin—simply serrate.

*Color.*—Mature: Upper surface—near Spinach Green, Plate 0960, but somewhat darker; under surface—near Spinach Green, Plate 0960/2.

Young: Upper surface—Spinach Green, Plate 0960/1; under surface—near Spinach Green, Plate 0960/2.

*Rachis (the supporting stem of the compound leaf).*—Upper side—smooth; grooved. Under side—Sparsely prickly, and usually having from 4 to 6 small prickles.

*Stipules.*—Medium length; medium width; with long points turning out at an angle of more then 45°.

*Disease resistance.*—Very resistant tc mildew, as compared with other varieties grown under comparable cultural conditions at Livermore, California.

Growth:

*Habit.*—Bushy; upright; much-branched.

*Growth.*—Very vigorous.

*Canes.*—Heavy.

*Main stems.*—Color—Scheele's Green, Plate 860/1. Thorns—many; long; hooked downward; with long, narrow base. Prickles—none. Hairs—none.

*Branches.*—Color—Scheele's Green, Plate 860/1. Thorns—several; medium length; hooked downward; with long, narrow base. Prickles—none. Hairs—none.

*New shoots.*—Color—Scheele's Green, Plate 860/1, heavily tinged with anthocyanin pigment where exposed to sun. Thorns—many; long; from straight to slightly hooked downward; with long, narrow base. Prickles—none. Hairs—none.

I claim:

A new and distinct variety of rose plant of the ever-blooming pillar rose type and the hybrid Wichuraiana class, substantially as herein shown and described, characterized particularly as to novelty by its general resemblance to the variety "High Noon" (Plant Patent No. 704), but being distinguished therefrom by its greater winter-hardiness, its larger, more glossy and more abundant foliage which better clothes the plant particularly near the base thereof, its larger and longer buds which are urn-shaped at first but become long-pointed and high-centered as the flowers open, its lighter colored buds which are Empire Yellow in general color tonality and have only a slight tinge of Maize Yellow color, and its lighter Yellow open flowers which are Empire Yellow in general color tonality.

No references cited.